United States Patent
Bahmer

(10) Patent No.: US 9,674,621 B2
(45) Date of Patent: *Jun. 6, 2017

(54) AUDITORY PROSTHESIS USING STIMULATION RATE AS A MULTIPLE OF PERIODICITY OF SENSED SOUND

(71) Applicant: MED-EL Elektromedizinische Geraete GmbH, Innsbruck (AT)

(72) Inventor: Andreas Bahmer, Aschaffenburg (DE)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 12 days.

This patent is subject to a terminal disclaimer.

(21) Appl. No.: 14/461,503

(22) Filed: Aug. 18, 2014

(65) Prior Publication Data

US 2015/0051668 A1 Feb. 19, 2015

Related U.S. Application Data

(60) Provisional application No. 61/867,200, filed on Aug. 19, 2013, provisional application No. 62/006,946, filed on Jun. 3, 2014.

(51) Int. Cl.
*A61N 1/36* (2006.01)
*H04R 25/00* (2006.01)
*A61N 1/05* (2006.01)

(52) U.S. Cl.
CPC ....... *H04R 25/505* (2013.01); *A61N 1/36032* (2013.01); *A61N 1/0541* (2013.01)

(58) Field of Classification Search
CPC .......................... A61N 1/0541; A61N 1/36032
See application file for complete search history.

(56) References Cited

U.S. PATENT DOCUMENTS 7,920,923 B2    4/2011   Laback et al. ................. 607/57
8,295,937 B2    10/2012  Fridman et al. ............... 607/57
(Continued)

FOREIGN PATENT DOCUMENTS

WO    WO 02/096153    11/2002    ............. H04R 25/00

OTHER PUBLICATIONS

Kitazawa et al., "Acoustic simulation of auditory model based speech processor for cochlear implant system", Proc. of the Int. Conf. on Spoken Language Processing, ICSLP'94, pp. 2043-2046 (1994).*

(Continued)

*Primary Examiner* — Eric D. Bertram
(74) *Attorney, Agent, or Firm* — Sunstein Kann Murphy & Timbers LLP

(57) ABSTRACT

A method is described for an auditory prosthesis system to generate electrical stimulation signals to stimulation contacts on an outer surface of an implanted electrode array. An input audio signal having a prominent sensed frequency is pre-processed to produce multiple representative frequency band signals. Each of the frequency band signals is then processed to generate corresponding electric stimulation signals for the stimulation contacts. Each of the electric stimulation signals has an associated stimulation frequency, and for at least one of the electric stimulation signals, the stimulation frequency is varied to maintain an integer ratio between the stimulation frequency and the prominent sensed frequency of the input audio signal.

10 Claims, 4 Drawing Sheets

(56) References Cited

U.S. PATENT DOCUMENTS

| | | | |
|---|---|---|---|
| 2005/0271222 A1 | 12/2005 | Freed et al. | 381/93 |
| 2008/0300653 A1 | 12/2008 | Svirsky | 607/57 |
| 2009/0187237 A1* | 7/2009 | Fridman | A61N 1/36032 607/137 |
| 2009/0254150 A1 | 10/2009 | Zierhofer | 607/57 |
| 2011/0286618 A1* | 11/2011 | Vandali et al. | 381/320 |
| 2011/0295331 A1 | 12/2011 | Wells et al. | 607/3 |
| 2012/0029593 A1 | 2/2012 | Calle et al. | 607/57 |

OTHER PUBLICATIONS

Bronkhorst, et al, "The effect of head-induced interaural time and level differences on speech intelligibility in noise", *J. Acoust. Soc. Am*, vol. 83, No. 4, Apr. 1988, pp. 1508-1516, 9 pages.

Buell, et al, "Discrimination of interaural differences of time in the envelopes of high-frequency signals: Integration times", *J. Acoust. Soc. Am.*, vol. 84, No. 6, Dec. 1988, pp. 2063-2066, 4 pages.

Colburn, et al, "Binaural Directional Hearing—Impairments and Aids", *Directional Hearing*, 1987, pp. 261-278.

Durlach, et al, "Binaural Interaction in Impaired Listeners", *Audiology*, 20: (1981), pp. 181-211, 31 pages.

Gabriel, Kaigham J., "Frequency dependence of binaural performance in listeners with impaired binaural hearing", *J. Acoust. Soc. Am*, vol. 91, No. 1, Jan. 1992, pp. 336-347, 12 pages.

Hafter, et al, "Detection of interaural differences of time in trains of high-frequency clicks as a function of interclick interval and number", *J. Acoust. Soc. Am*, vol. 73, No. 2, Feb. 1983, pp. 644-651, 8 pages.

Hawkins, et al, "Interaural Time Discrimination Ability of Listeners with Sensorineural Hearing Loss", *Audiology*, vol. 19, (1980), pp. 495-507, 13 pages.

Kaibao, N., et al, "Encoding Frequency Modulation to Improve Cochlear Implant Performance in Noise", *IEEE Transactions on Biomedical Engineering*, vol. 52, No. 1, Jan. 2005, pp. 64-73, 10 pages.

Koehnke, et al, "Effects of Reference Interaural Time and Intensity Differences on Binaural Performance in Listeners with Normal and Impaired Hearing", *Ear & Hearing*, vol. 16, No. 4, pp. 331-353, 23 pages.

Koehnke, et al, "Binaural Performance in Listeners With Impaired Hearing: Aided and Unaided Results", *Binaural and spatial Hearing in Real and Virtual Environments*, R. Gilkey 7 T. Anderson eds., Erlbaum, Hillsdale, NJ, Chapter 33, pp. 725-751, 14 pages.

Laback, et al, "Binaural jitter improves interaural time-difference sensitivity of cochlear implantees at high pulse rates", *PNAS*, vol. 105, No. 2., Jan. 15, 2008, pp. 814-817, 4 pages.

Laback, et al, "Lateralization discrimination of interaural time delays in four-pulse sequences in electric and acoustic hearing", *J. Acoust. Soc. Am*, vol. 121, No. 4, Apr. 2007, pp. 2182-2191, 10 pages.

Litvak, et al, "Auditory nerve fiber responses to electric stimulation: Modulated and unmodulated pulse trains", *J. Acoust. Soc. Am*, vol. 110, No. 1, Jul. 2001, pp. 368-379, 12 pages.

Macpherson, et al, "Listener weighting of cues for lateral angle: The duplex theory of sound localization revisited", *J. Acoust. Soc. Am*, vol. 111, No. 5, Pt. 1, May 2002, pp. 2219-2236, 18 pages.

Majdak, et al, "Effects of interaural time differences in fine structure and envelope on lateral discrimination in electric hearing", *J. Acoust. Soc. Am*, vol. 120, No. 4, Oct. 2006, pp. 2190-2201, 12 pages.

Saberi, Kourosh, "Observer weighting of interaural delays in filtered impulses", *Perception & Psychophysics*, 58, (7), 1996, pp. 1037-1046, 10 pages.

Smith, et al, "Chimaeric sounds reveal dichotomies in auditory perception", *Nature*, Mar. 7, 2002; 416(6876), pp. 87-90, 10 pages.

Smoski, et al, "Discrimination of interaural temporal disparities by normal-hearing listeners and listeners with high-frequency sensorineural hearing loss", *J. Acoust. Soc. Am.*, vol. 79, No. 5, May 1986, pp. 1541-1547, 7 pages.

Stecker, G. C., et al, "Temporal weighting in sound localization", *J. Acoust. Soc. Am*, vol. 122, No. 3, Pt. 1, Sep. 2002, pp. 1046-1057, 12 pages.

Van Hoesel, et al, "Speech perception, localization and laterization with bilateral cochlear implants", *J. Acoust. Soc. Am.* vol. 113, No. 3, Mar. 2003, pp. 1617-1630, 14 pages.

Van Hoesel, Richard J. M., "Sensitivity to binaural timing in bilateral cochlear implant users", *J. Acoust. Soc. Am*, vol. 121, No. 4, Apr. 2007, pp. 2192-2206, 15 pages.

Wightman, et al, "Factors Affecting the Relative Salience of Sound Localization Cues", *Gikey and Anderson*, [20], 1997, Chapter 1, pp. 1-23, 12 pages.

Zeng, et al, "Speech recognition with amplitude and frequency modulations", *PNAS*, vol. 102, No. 7, Feb. 15, 2005, pp. 2293-2298, 6 pages.

International Searching Authority, Authorized Officer Dana Schalinatus, International Search Report and Written Opinion PCT/EP2008/004959, date of mailing Aug. 25, 2008, 14 pages.

International Searching Authority, Authorized Officer Shane Thomas, International Search Report and Written Opinion PCT/US14/51409, date of mailing Dec. 9, 2014, 18 pages.

* cited by examiner

AUDITORY PROSTHESIS USING STIMULATION RATE AS A MULTIPLE OF PERIODICITY OF SENSED SOUND

This application claims priority from U.S. Provisional Patent Application 61/867,200, filed Aug. 19, 2013, and from U.S. Provisional Patent Application 62/006,946, filed Jun. 3, 2014, which are incorporated herein by reference in their entireties.

FIELD OF THE INVENTION

The present invention relates to medical implants, and more specifically to electric stimulation techniques in cochlear implant systems and other implantable auditory prostheses.

BACKGROUND ART

A normal human ear transmits sounds as shown in FIG. 1 through the outer ear 101 to the tympanic membrane 102 which moves the bones of the middle ear 103 that vibrate the oval window and round window openings of the cochlea 104. The cochlea 104 is a long narrow duct wound spirally about its axis for approximately two and a half turns. It includes an upper channel known as the scala vestibuli and a lower channel known as the scala tympani, which are connected by the cochlear duct. The cochlea 104 forms an upright spiraling cone with a center called the modiolar where the spiral ganglion cells of the acoustic nerve 113 reside. In response to received sounds transmitted by the middle ear 103, the fluid-filled cochlea 104 functions as a transducer to generate electric pulses which are transmitted to the cochlear nerve 113, and ultimately to the brain.

Hearing is impaired when there are problems in the ability to transduce external sounds into meaningful action potentials along the neural substrate of the cochlea 104. To improve impaired hearing, auditory prostheses have been developed. For example, when the impairment is related to operation of the middle ear 103, a conventional hearing aid may be used to provide acoustic-mechanical stimulation to the auditory system in the form of amplified sound. Or when the impairment is associated with the cochlea 104, a cochlear implant with an implanted electrode can electrically stimulate auditory nerve tissue with small currents delivered by multiple electrode contacts distributed along the electrode. Although the following discussion is specific to cochlear implants, some hearing impaired persons are better served when the stimulation electrode is implanted in other anatomical structures. Thus auditory prostheses systems include brainstem implants, middle brain implants, etc. each stimulating a specific auditory target in the hearing system.

FIG. 1 also shows some components of a typical cochlear implant system where an external microphone provides an audio signal input to an external signal processor 111 in which various signal processing schemes can be implemented. For example, signal processing approaches that are well-known in the field of cochlear implants include continuous interleaved sampling (CIS) digital signal processing, channel specific sampling sequences (CSSS) digital signal processing (as described in U.S. Pat. No. 6,348,070, incorporated herein by reference), spectral peak (SPEAK) digital signal processing, fine structure processing (FSP) and compressed analog (CA) signal processing.

The processed signal is then converted into a digital data format for transmission by external transmitter coil 107 into the implant 108. Besides receiving the processed audio information, the implant 108 also performs additional signal processing such as error correction, pulse formation, etc., and produces a stimulation pattern (based on the extracted audio information) that is sent through an electrode lead 109 to an implanted electrode array 110. Typically, this electrode array 110 includes multiple electrode contacts 112 on its surface that provide selective stimulation of the cochlea 104.

FIG. 2 shows various functional blocks in a typical CI signal processing system using the CIS stimulation strategy. A sound pre-processor 201 includes a pre-emphasis filter 203 that receives an audio signal from a microphone and attenuates strong frequency components in the audio signal below about 1.2 kHz. FIG. 3 shows a typical example of a short time period of an audio signal from a microphone. The sound pre-processor 201 also includes multiple band-pass filters (BPFs) 204 that decompose the audio signal from the pre-emphasis filter 203 into multiple spectral bands as shown, for example, in FIG. 4. A sound processor 202 includes envelope detectors 205 that extract the slowly-varying envelopes of the spectral band signals, for example, by full-wave rectification and low pass filtering. The sound processor 202 also includes a non-linear (e.g., logarithmic) mapping module 206 that performs compression of the envelopes to fit the patient's perceptual characteristics, and the compressed envelope signals are then multiplied with carrier waveforms by modulators 207 to produce electric stimulation signals in the specific form of non-overlapping biphasic output pulses for each of the stimulation electrodes (EL-1 to EL-n) implanted in the cochlea.

CIS stimulation imposes a fixed stimulation rate on the delivered electrical pulses and therefore cannot represent periodicity components of the sensed audio signal. On the other hand, FSP stimulation (and its variants) does represent the inherent periodicity of sensed audio signals. FSP generates stimulation pulse trains responsive to detection of specific pre-defined signal characteristics such as zero crossing events. But FSP pulse trains after zero crossing events can only be presented in a pre-defined pattern. That means that the time period between the actual zero crossing and the initial pulse of the pulse trains may be different for each zero crossing event, thereby introducing unwanted jitter.

In contrast to the case of unwanted signal jitter, U.S. Pat. No. 7,920,923 describes intentionally introducing a random artificial phase jitter component to binaural stimulation signals. This is done to reduce the periodic characteristics of the fine structure component while preserving interaural time difference (ITD) information.

SUMMARY OF THE INVENTION

Embodiments of the present invention are directed to generating electrical stimulation signals for the stimulation contacts on an outer surface of an implanted electrode array. An input audio signal having a prominent sensed frequency is pre-processed to produce multiple representative frequency band signals. Each of the frequency band signals is then processed to generate corresponding electric stimulation signals for the stimulation contacts. Each of the electric stimulation signals has an associated stimulation frequency, and for at least one of the electric stimulation signals, the stimulation frequency is varied to maintain an integer ratio between the stimulation frequency and the prominent sensed frequency of the input audio signal.

In specific embodiments, the frequency band signals may be produced by a bank of band pass filters each associated with a corresponding audio frequency band. For each of the electric stimulation signals, the stimulation frequency may be varied to maintain an integer ratio between the stimulation frequency and the sensed frequency of the input audio signal.

The prominent sensed frequency of the input audio signal may be a fundamental frequency and/or a harmonic of a fundamental frequency of the input audio signal. Or the prominent sensed frequency of the input audio signal may be a most prominent frequency of a broadband filter signal. The prominent sensed frequency may be determined using a fast Fourier transform.

In specific applications, the stimulation frequency may be varied as a function of a music processing mode and/or a target audio source processing mode of the auditory prosthesis system.

DETAILED DESCRIPTION OF SPECIFIC EMBODIMENTS

Figure 5:
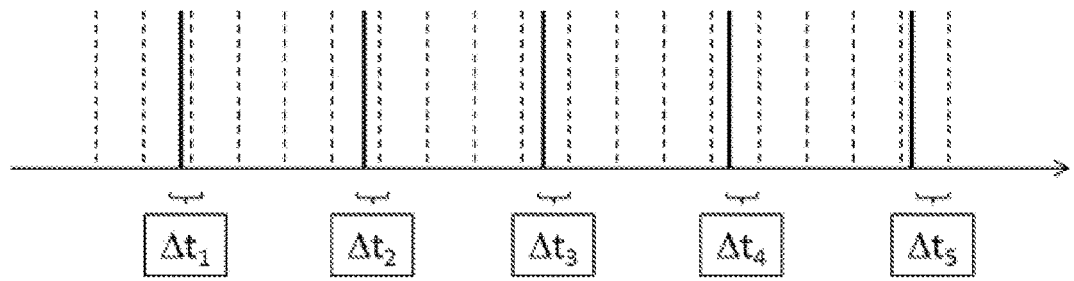
FIG. 5 illustrates the problem of varying jitter between stimulation signals and sensing pattern.

As discussed above, representation of the periodicity in an analog signal by a discrete system is inherently limited by its temporal resolution. For cochlear implants, this means that the highest stimulation rate (which is usually also the highest sensing rate) is the limit for the temporal resolution. If the input audio signal has a periodicity with a frequency f(a) and the sensing/stimulation rate of the CI system has a frequency f(e), a beating characterized by both frequencies is generated. Consequently, the electrical pulses may carry a jitter with respect to the zero crossing events. FIG. 5 illustrates this problem of the varying jitter between stimulation signals (solid lines) and sensing pattern (dashed lines). One way to reduce the problem of such jitter is to increase the sensing/stimulation rate. But that is rather energy consuming and ultimately has other technical limitations.

Figure 1:
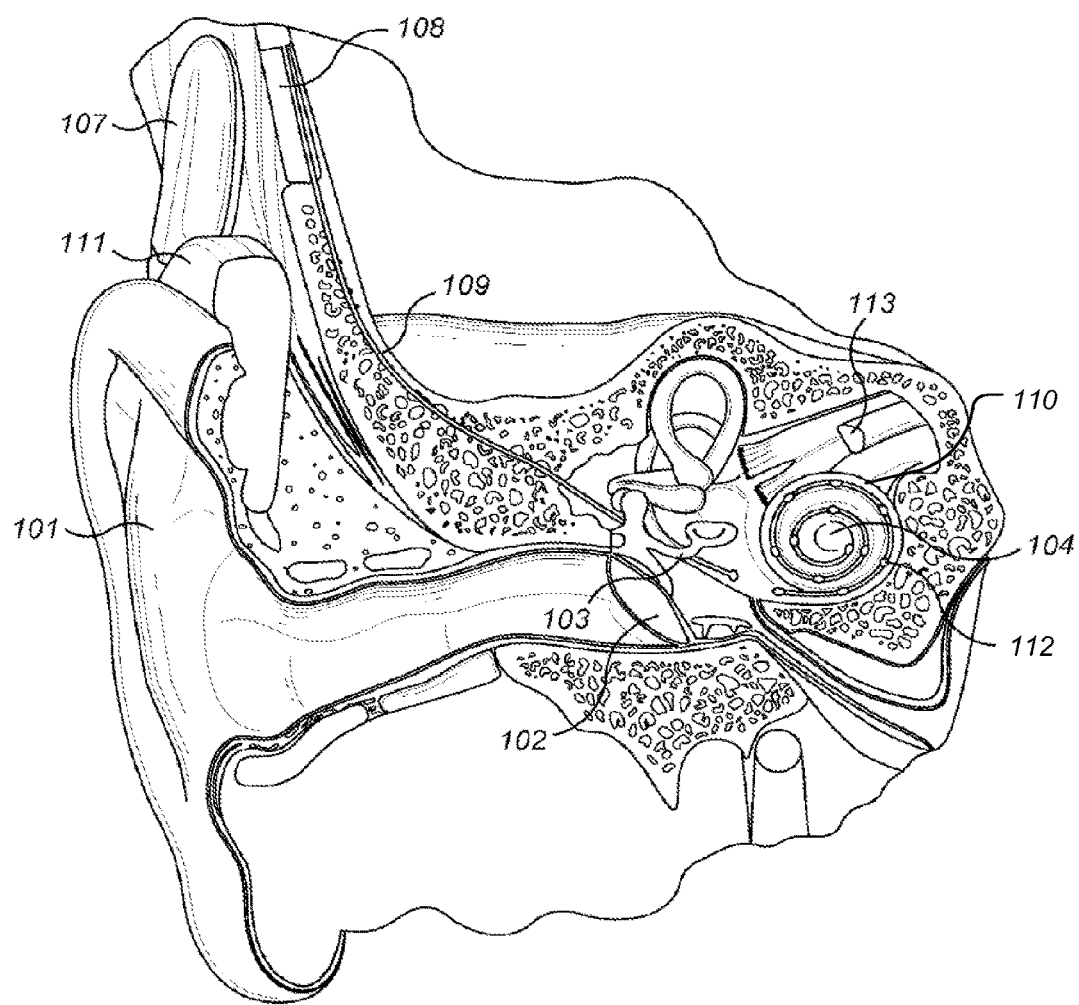
FIG. 1 shows a section view of a human ear with a typical auditory prosthesis system designed to deliver electric stimuli to the inner ear and acoustic stimuli at the ear canal.
Figure 2:
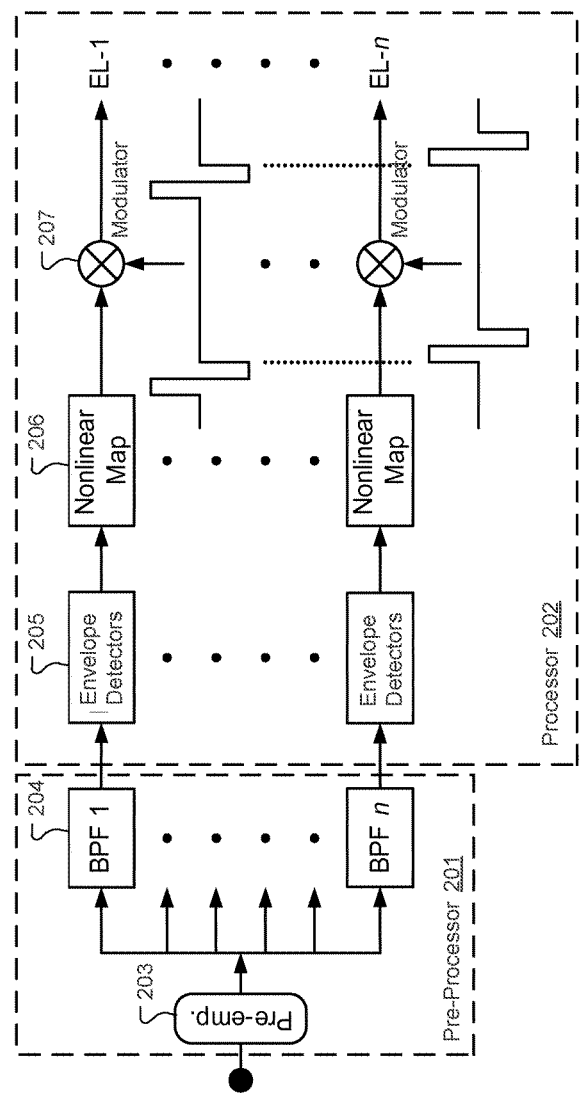
FIG. 2 shows various functional blocks in a continuous interleaved sampling (CIS) processing system.
Figure 3:
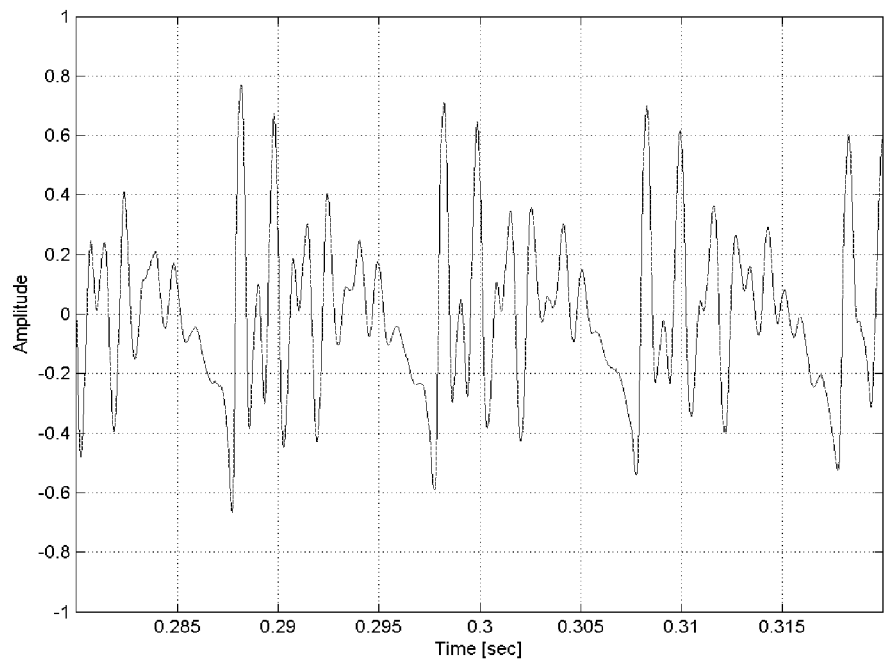
FIG. 3 shows an example of a short time period of an audio speech signal from a microphone.
Figure 4:
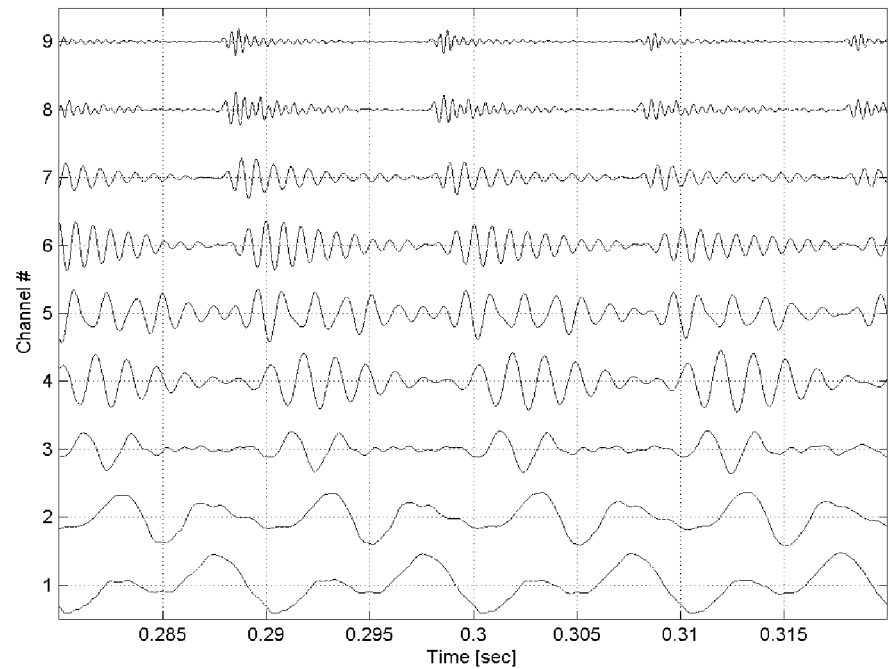
FIG. 4 shows an acoustic microphone signal decomposed by band-pass filtering by a bank of filters into a set of signals.

Embodiments are directed to reducing or eliminating unwanted jitter in auditory prostheses such as cochlear implants. In a CI signal processing system such as the one shown in FIG. 2, the sound processor 202 varies the stimulation frequency for at least one of the electric stimulation signal channels to maintain an integer ratio between the stimulation frequency and the prominent sensed frequency of the input audio signal. That is, for at least one of the electrode stimulation channels, the sound processor 202 changes the sensing/stimulation rate f(e) from a fixed one to a variable one such that it is in an integer relation to the prominent sensed frequency f(a) of the input audio signal, i.e. f(e)=n times f(a) where n may be an integer or a quotient of integers.

The prominent sensed frequency f(a) may be without limitation the fundamental frequency of the input audio signal, a harmonic of the fundamental frequency of the input audio signal, or simply the most prominent frequency of a pre-defined band filter such as from a low frequency broadband filter as described, e.g., in U.S. Patent Publication 2009/0254150, which is incorporated herein by reference. A broadband coherent mixing arrangement as described in U.S. Patent Publication 2009/0254150 may be advantageous as compared to a system based on determining the fundamental frequency of the input audio signal since it may be very difficult in many real-life hearing situations to unambiguously determine a fundamental frequency. Alternatively or in addition, the prominent sensed frequency may also be determined via performing an FFT of the input audio signal.

In some embodiments, multiple stimulation signal channels may have their stimulation frequency varied to maintain an integer ratio between the stimulation frequency and the prominent sensed frequency of the input audio signal. This may be especially useful, for example, in situations when a cochlear implant user listens to sounds that carry a well-defined fundamental frequency and corresponding harmonics as when listening to music. Thus embodiments of the present invention include cochlear implant systems which have a music processing mode in which the stimulation frequency may be varied to eliminate jitter, and which may be user selectable or automatically selected by the system when appropriate. If the cochlear implant user is in a situation where the system cannot reliably detect a prominent sensed frequency, the system may just switch to another normal stimulation mode and/or a previously selected stimulation rate may be maintained.

Figure 6:
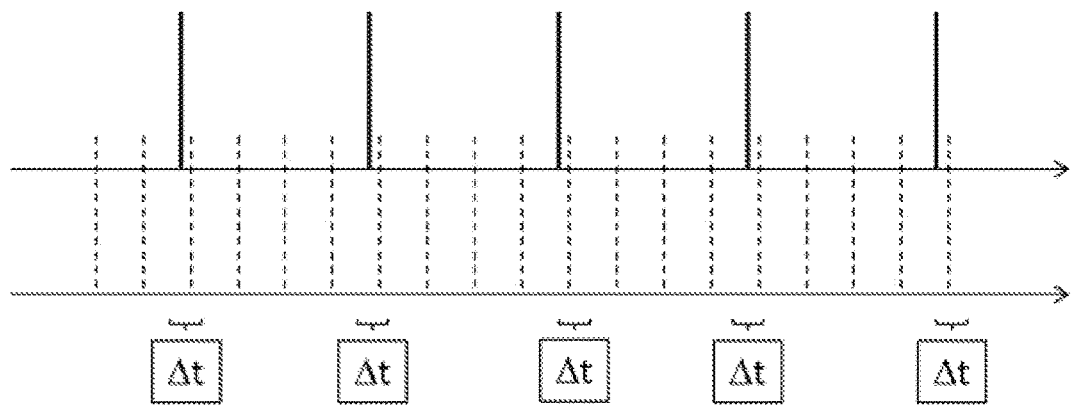
FIG. 6 illustrates stimulation signals and sensing pattern with a constant time offset without jitter as produced by an embodiment of the present invention.
Figure 7:
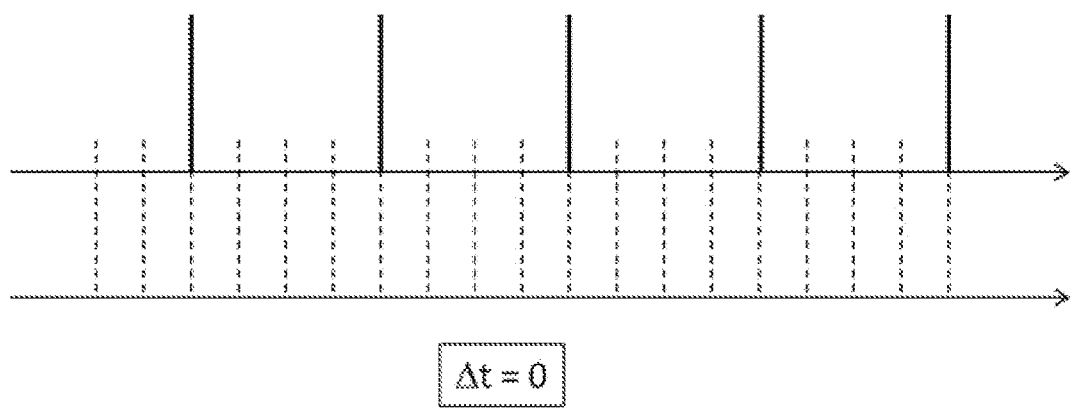
FIG. 7 illustrates stimulation signals and sensing pattern with zero time offset without jitter as produced by an embodiment of the present invention.

Varying the stimulation frequency as described above effectively eliminates the jitter seen in FIG. 5. As shown in FIG. 6, the stimulation frequency can be varied to maintain a constant duration offset between the stimulation signal (solid lines) and the prominent sensed frequency (dashed lines). Or as shown in FIG. 7, an embodiment may control the stimulation frequency with respect to the prominent sensed frequency to have zero offset, and inherently thereby, zero jitter. And, while the foregoing discussion is presented in terms of integer stimulation ratios of stimulation frequencies, of course it also applies to integer values of corresponding time periods.

One advantage of embodiments of the present invention is that the prominent sensed frequency signal which determines the stimulation rate is more pronounced while other pattern frequencies that may be present in the input audio signal are less represented. So this approach to controlling jitter also introduces a filter function for the signal of interest. This may be helpful in some situations such as where multiple people are speaking at the same time. And if a cochlear implant system utilizes directional microphone characteristics, the representation of a targeted speaker's voice may be enhanced while the other speaker voices are attenuated. Thus some embodiments of the present invention may have a target audio source processing mode for such circumstances that eliminates jitter and enhances the prominent frequency of the targeted speaker.

In addition, elimination of unwanted jitter as described above also may be useful or necessary for further processing in specific systems which introduce intentional jitter such as described in U.S. Patent Publication 2008/0319509 and U.S.

Provisional Patent Application 61/720,600, filed Oct. 31, 2012, which are incorporated herein by reference.

Besides hearing prosthesis systems such as cochlear implants, embodiments of the present invention can be implemented in a deep brain stimulation (DBS) system. A DBS system in such an embodiment generates electrical stimulation signals for a one or more stimulation contacts on an outer surface of an electrode array that is implanted in a deep brain stimulation system location as is known in the art. A basic frequency is determined and electric stimulation signals are generated for each stimulation contact, each stimulation signal having a determined operating stimulation frequency. For at least one of the electric stimulation signals, the operating stimulation frequency is varied to maintain an integer ratio between the operating stimulation frequency and the basic frequency.

In such an embodiment, there are various specific ways to determine the basic frequency, including without limitation deriving a frequency from a recorded EEG measurement, deriving a frequency from an intra-operative (objective) response measurement of neural brain tissue, or just defining a frequency based on the experience of a medical expert, etc. Similarly, the operating stimulation frequency also may be determined in various specific ways, including without limitation a frequency derived from a recorded EEG measurement, a frequency derived from an intraoperative (objective) response measurement of neural brain tissue, or just a frequency defined based on the experience of a medical expert, etc. In addition the operating frequency may also be derived from an (objective) response measurement of neural brain tissue for each electrode contact after implantation, which would allow a closed loop system where the operating stimulation frequency may be (automatically) adjusted from time to time according to the (objective) response measurement.

Embodiments of the invention may be implemented in part in any conventional computer programming language. For example, preferred embodiments may be implemented in a procedural programming language (e.g., "C") or an object oriented programming language (e.g., "C++" or Python). Alternative embodiments of the invention may be implemented as pre-programmed hardware elements, other related components, or as a combination of hardware and software components.

Embodiments can be implemented in part as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Although various exemplary embodiments of the invention have been disclosed, it should be apparent to those skilled in the art that various changes and modifications can be made which will achieve at least some of the advantages of the invention without departing from the true scope of the invention. For example, the approaches described herein could be applied for auditory prostheses other than cochlear implants such as an auditory brainstem implant with the electrical stimuli presented by electrodes within or adjacent to the cochlear nucleus, or an auditory midbrain implant with the electrical stimuli presented by electrodes on or within the inferior colliculus.

What is claimed is:

1. A method of an auditory prosthesis system for generating electrical stimulation signals for a plurality of stimulation contacts on an outer surface of an implanted electrode array, the method comprising:
pre-processing an input audio signal having a prominent sensed frequency representing a fundamental frequency of the input audio signal to produce a plurality of representative frequency band signals; and
processing each of the frequency band signals to generate a corresponding plurality of electric stimulation signals for the stimulation contacts, each electric stimulation signal having an associated stimulation pulse frequency, wherein for at least a selected one of the electric stimulation signals, the stimulation pulse frequency is varied to be maintained at an integer multiple greater than the prominent sensed frequency of the input audio signal.

2. A method according to claim 1, wherein the frequency band signals are produced by a bank of band pass filters each associated with a corresponding audio frequency band.

3. A method according to claim 1, wherein for each of the electric stimulation signals the stimulation pulse frequency is varied to be maintained at an integer multiple greater than the prominent sensed frequency of the input audio signal.

4. A method according to claim 1, wherein varying the stimulation pulse frequency is performed as a function of a music processing mode of the auditory prosthesis system.

5. A method according to claim 1, wherein varying the stimulation pulse frequency is performed as a function of a target audio source processing mode of the auditory prosthesis system.

6. An auditory prosthesis system comprising:
an implanted electrode array having an outer surface with a plurality of stimulation contacts;
a sound pre-processor configured for initial pre-processing of an input audio signal having a prominent sensed frequency representing a fundamental frequency of the input audio signal to produce a plurality of representative frequency band signals; and
a signal processor configured for processing each of the frequency band signals to generate a corresponding plurality of electric stimulation signals for the stimulation contacts, each electric stimulation signal having an associated stimulation pulse frequency, wherein for at least a selected one of the electric stimulation signals, the signal processor varies the stimulation pulse frequency to be maintained at an integer multiple greater than the prominent sensed frequency of the input audio signal.

7. A system according to claim 6, further comprising:
a bank of band pass filters each associated with a corresponding audio frequency band configured for producing the band pass signals.

8. A system according to claim 6, wherein the signal processor is configured to vary the stimulation pulse rate of each of the electric stimulation signals to be maintained at an integer multiple greater than the prominent sensed frequency of the input audio signal.

9. A system according to claim 6, wherein the signal processor is configured to use a music processing mode for varying the stimulation pulse frequency.

10. A system according to claim 6, the signal processor is configured to use a target audio source processing mode for varying the stimulation pulse frequency.

* * * * *